United States Patent [19]

Rosensaft et al.

[11] 4,300,565

[45] Nov. 17, 1981

[54] SYNTHETIC POLYESTER SURGICAL ARTICLES

[75] Inventors: Michael N. Rosensaft, Monsey, N.Y.; Richard L. Webb, Darien, Conn.

[73] Assignee: American Cyanamid Company, Stamford, Conn.

[21] Appl. No.: 191,655

[22] Filed: Sep. 26, 1980

Related U.S. Application Data

[60] Continuation-in-part of Ser. No. 143,978, Apr. 28, 1980, which is a division of Ser. No. 960,264, Nov. 13, 1978, which is a continuation-in-part of Ser. No. 799,836, May 23, 1977, abandoned.

[51] Int. Cl.³ ............... A61L 17/00; C08G 63/08; C08L 67/04
[52] U.S. Cl. ................ 128/335.5; 525/415; 528/354
[58] Field of Search ............ 128/335.5; 525/415; 528/354

[56] References Cited

U.S. PATENT DOCUMENTS

| | | | |
|---|---|---|---|
| 3,784,585 | 1/1974 | Schmitt | 528/354 |
| 3,839,297 | 10/1974 | Wasserman | 528/354 |
| 3,867,190 | 2/1975 | Schmitt | 128/355.5 |
| 3,875,937 | 4/1975 | Schmitt | 128/156 |
| 3,896,802 | 7/1975 | Williams | 128/156 |
| 3,937,223 | 2/1976 | Roth | 128/325 |
| 4,033,938 | 7/1977 | Augurt | 528/354 |
| 4,045,418 | 8/1977 | Sinclair | 528/354 |
| 4,057,537 | 11/1977 | Sinclair | 528/354 |
| 4,137,921 | 2/1979 | Okuzumi | 260/823 |
| 4,157,437 | 6/1979 | Okuzumi | 260/823 |
| 4,190,655 | 2/1980 | Shalaby | 528/354 |

*Primary Examiner*—Paul Lieberman
*Attorney, Agent, or Firm*—Charles F. Costello, Jr.

[57] ABSTRACT

A procedure is disclosed employing the sequential addition of monomers to form a copolymer useful in the manufacture of surgical articles.

17 Claims, No Drawings

SYNTHETIC POLYESTER SURGICAL ARTICLES

CROSS-REFERENCE TO RELATED APPLICATIONS

This is a continuation-in-part application of U.S. application, Ser. No. 143,978 filed Apr. 28, 1980, which is a divisional of U.S. application, Ser. No. 960,264 filed Nov. 13, 1978, which is a continuation-in-part of U.S. application, Ser. No. 799,836 filed May 23, 1977 now abandoned.

BACKGROUND OF THE INVENTION

This invention relates to a new and useful method for preparing synthetic polyester surgical articles, as well as the articles produced thereby and methods for using them.

The use of cyclic ester monomers in the formation of polyesters for the fabricating of synthetic surgical articles is well known in the art. In conjunction therewith, comonomers have often been employed to modify the characteristics of the various polyesters.

The conventional polymerization method for forming polymers of the cyclic esters is through ring opening polymerizations. Usually, where copolymers are prepared, one cyclic ester is copolymerized with another.

The use of monomers in the formation of polyester surgical articles is discussed in a variety of patents and technical publications. Useful polymerization and post-treatment methods as well as fabrication procedures for the surgical articles are also well known. The surgical articles produced include both absorbable and non-absorbable articles.

The following patents and technical articles and references cited therein are of interest in this respect:
(1) U.S. Pat. Nos.—3,268,486-7; 3,297,033; 3,442,871; 3,463,158; 3,620,218; 3,626,948; 3,739,773; 3,839,297; 3,875,937; 3,896,802; 3,937,223; 3,728,839; 3,531,561; 3,867,190; 3,784,585.
(2) Foreign Pat. Nos.—1,332,505; 1,414,600 (British), and 776,980; 778,126; 788,116 (Belgian).
(3) Technical Articles—Developement of a Synthetic Polymer Burn Covering; by John B. Gregory et al; DYNATECH R/D COMPANY in conjunction with Department of the Navy, Contract No. N00014-73-C-0201; March 30, 1973;

Developement of a Synthetic Polymer Burn Covering; by John B. Gregory et al; DYNATECH R/D COMPANY in conjunction with Department of the Navy, Contract No. N00014-73-C-0201; June 8, 1973;

Developement of a Synthetic Polymer Burn Covering; by A. D. Schwope et al; DYNATECH CORPORATION in conjunction with Department of the Navy, Contract Authority NR 104-702/10-3-72 (444); January 31, 1974.

D. E. Cutright et al, Oral Surg. Vol. 31, No. 1, p. 134–9, Jan. 1971; Vol. 32 No. 1, p. 165–173, July 1971 and Vol. 37, No. 1, p. 142–152, January 1974.

July 25, 1972, Report by R. G. Sinclair and G. W. Gynn entitled Preparation and Evaluation of Glycolic and Lactic Acid Based Polymers For Implant Devices Used In Management of Maxillofacial Trauma, published in conjunction with Contract No. DADA17-72-C-2066. Supported by the U.S. Army Medical Research and Development Command.

As mentioned as conjunction with U.S. Pat. No. 3,867,190 and its parent patent applications the biological inertness of the polylactic acid sutures prepared with the hope of being absorbable in living tissue was modified by incorporation of glycolic acid units in the polymer chain. Unfortunately, the copolymers formed by coreacting increasing amounts of glycolide with the lactide were said to have the disadvantage of forming surgical articles which lacked dimensional stability in-vivo.

SUMMARY OF THE INVENTION

This invention describes an improved method for the manufacture of sterile surgical articles fabricated from a synthetic absorbable copolymer formed by copolymerizing glycolide monomer with a cyclic ester monomer other than glycolide. The improvement comprises employing sequential addition of the monomers in the polymerization, wherein the glycolide monomer, the cyclic ester monomer, or a combination of the monomers is substantially completely polymerized before the addition of the other monomer or combination. In the preferred method the cyclic ester monomer is lactide. In the most preferred method, the lactide is L(—)lactide.

In another preferred method the cyclic ester monomer is selected from the group consisting of lactones, oxalates or carbonates. In the most preferred method, the cyclic ester monomer is 1,4-dioxane-2,3-dione or 1,3-dioxane-2-one.

This invention also describes a sterile surgical article fabricated from a synthetic absorbable copolymer prepared according to the method described above. In a preferred embodiment, the sterile surgical article is in the form of a suture or a ligature. In a most preferred embodiment, the sterile surgical article is in the form of a needle and suture combination.

This invention also describes a copolymer comprising a proportion of sequential units having the formula:

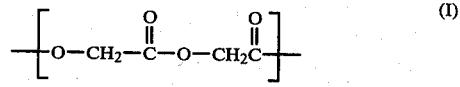

and a proportion of sequential units having the formula:

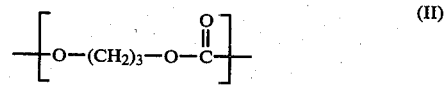

The end groups which could be used with this copolymer are well known in the art. These end groups include, but are not limited to, lauryl, hydroxyl and carboxyl. A preferred copolymer has a melting point of about 217° C. to 221° C. as described by the peak in a differential scanning calorimeter operating at a heating rate of 10° C. per minute. In addition to the melting point characteristic, another embodiment is a copolymer having an inherent viscosity of about 0.5 dl/g. (deciliter per gram) to 2 dl/g. Still another embodiment is a copolymer having an inherent viscosity of about 0.7 dl/g to 1.2 dl/g.

Within the scope of this invention is a copolymer described above wherein formula (II) consists of between about 1% to 99% by weight. A narrower embodiment is a copolymer described above wherein formula (II) consists of up to about 50% by weight. Another embodiment is a copolymer described above wherein formula (II) consists of up to about 35% by weight. Still another embodiment is a copolymer described above wherein formula (II) consists of between about 10% to 20% by weight.

Also within the scope of this invention is a sterile surgical article fabricated from a synthetic absorbable copolymer as described above. In a preferred embodiment, the sterile surgical article is in the form of a suture or ligature. In a most preferred embodiment, the sterile surgical article is in the form of a needle and suture combination.

A method of retaining living tissue in a desired relationship during a healing process by positioning and emplacing living tissue with a sterile surgical article fabricated from a synthetic absorbable copolymer as described above is also within the scope of this invention. Finally, a method of closing a wound of living tissue which comprises sewing the edges of the wound with a sterile surgical article in the form of a needle and suture combination as described above is within the scope of this invention.

DESCRIPTION OF THE INVENTION

It has now been found that synthetic polyester surgical articles can advantageously be manufactured by employing in conjunction therewith a polymerization procedure whereby a copolymer is formed through a ring opening polymerization wherein the polymerization is sequentially or incrementally carried out. This is achieved by consecutively adding the monomers used to form the copolymer chain. By conducting the polymerization procedure in a stepwise or staged manner, the in vivo characteristics of the surgical articles produced can more broadly be modified prior to encountering the usual degree in interference of the ability of the polymer to form dimensionally stable, highly crystalline, or highly oriented molecular structures.

The process of the present invention can be employed in two or more stages using two or more monomers in the polymerization procedure. In one or more of the stages, two monomers can be employed simultaneously. A different catalyst may be employed at each stage if desired.

It is generally preferred to conduct the consecutive polymerizations in the same reaction vessel by sequentially adding the monomers thereto; however, if desired one or more of the polymer segments can be prepared and used as such for further chemical reaction to form the final copolymer in a different reaction vessel of choice while still retaining the advantages of and falling within the present invention.

The two monomers conventionally preferred for use in preparing surgical articles are L(−) lactide and glycolide. They are also preferred for use in the present invention. Furthermore, it is generally preferred, herein, to employ them together in a sequential polymerization procedure. A second monomer pair preferred for use in the present invention is trimethylene carbonate/glycolide.

One or more of the following intramolecular cyclic esters may also be used as one of the monomers to copolymerize with glycolide in the practice of the present invention: β-propiolactone, β-butyrolactone, gamma-butyrolactone, 2-keto-1,4-dioxane, delta-valerolactone, epsilon-caprolactone, pivalolactone, α,α-diethylpropiolactone, 2,5-diketomorpholine, 6,8-dioxabicyclo[3,2,1]-octane-7-one, ethylene carbonate, ethylene oxalate, 3-methyl-1,4-dioxane-2,5-dione, 3,3-dimethyl-1,4-dioxane-2,5-dione; and intermolecular cyclic diesters of α-hydroxybutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-α-methyl-valeric acid, α-hydroxyheptanoic acid, α-hydroxyoctanoic acid, α-hydroxydecanoic acid, α-hydroxymyristic acid, α-hydroxystearic acid, α-hydroxylignoceric acid and salicylic acid.

As mentioned above, one of the preferred areas for use of the present invention relates to the preparation of sterile, synthetic, absorbable, surgical articles (especially sutures) wherein glycolide is employed as the predominant monomer in preparing the polyesters. The present state of the art is such that detailed absorption mechanisms and details of the polymer structures on the molecular levels are not known with certainty.

One of the preferred embodiments of the present invention relates to sequentially copolymerizing lactide [preferably L(−) lactide] with glycolide. Triblock structures formed by sequentially and consecutively copolymerizing L(−) lactide, glycolide and L(−) lactide respectively are also of interest. In the latter case, the copolymer produced has lactic acid units predominating on both ends of the glycolide polymer chain.

Another preferred embodiment of the present invention relates to copolymers of trimethylene carbonate and glycolide. Monofilament sutures fabricated from such copolymers have been found to be surprisingly useful in that they are more resistant to in-vivo strength loss than similar sutures fabricated from polyglycolide.

It is believed that the three usual morphological units, namely spheres, rods (or cylinders) and lamellae which are well known in AB and ABA type copolymers, e.g., poly(styrene-b-butadiene) (PSB) would be exhibited in the copolymers of the present invention. In films of PSB where the mole ratio of styrene units to butadiene units is 80/20, spherical domains have been observed by electron microscopy. As the mole ratio decreases with relatively greater quantities of butadiene units the morphology of the microphase separation is altered from spheres of butadiene units in a matrix of styrene units to rods of butadiene units in a matrix of styrene units and then to alternate lamellae of the units. When the mole ratio is further decreased until the butadiene predominates, the styrene units are first presented as a cylindrical or rod like microphase separations in a matrix of butadiene units whereafter, as the mole ratio is further decreased, the styrene units are presented as spheres in a matrix of butadiene units. (See M. Matsuo, S. Sagae and H. Asai, Polymer, 10, 79, 1969).

As mentioned above, in the preparation of absorbable sutures, in accordance with the practice of the present invention one may employ polyesters wherein minor amounts of a chain segment formed from another monomer such as L(−) lactide or trimethylene carbonate is incorporated at one or both ends of a chain of glycolide units.

It is to be understood that employing sequential addition of a cyclic ester other than glycolide which is substantially completely polymerized before the addition of glycolide is within the practice of the present invention. The addition of trimethylene carbonate followed by the addition of glycolide is preferred.

The surgical articles are fabricated from the copolymer using conventionally employed procedures. All of the above patents and technical articles are incorporated herein by reference. Likewise, the resulting surgical articles are employed in a conventional manner.

The following examples illustrate procedures which are useful in conjunction with the practice of the present invention but are not to be taken as being limiting thereof. Unless otherwise specified, all parts and percentages mentioned herein are by weight. In all of the examples, where not indicated, inherent viscosity (or I.V.) is measured using a solution of 0.5 grams of copolymer per 100 milliliters of hexafluoroacetone sesquihydrate (HFAS) at 30° C.

EXAMPLES 1-2

An ether solution of $SnCl_2.2H_2O$ and an ether solution of lauryl alcohol were prepared. A sufficient volume of the above solutions was added to two polymerization tubes so that when the solvent was removed the final weights of $SnCl_2.2H_2O$ and lauryl alcohol per 20.0 g of L(—) lactide monomer were as indicated in Table I:

TABLE I

| Tube No. | mg Sn $Cl_2$ . 2 $H_2O$ | mg Lauryl Alcohol |
|---|---|---|
| 1 | 2.0 | 125 |
| 2 | 4.0 | 250 |

After the solvent was removed, 20.0 g of L(—) lactide was added to each tube. The tubes were evacuated and sealed under vacuum. They were then placed in an oil bath at 180° C. for 24 hours. They were removed from the oil bath and let cool to room temperature. The tubes were opened, the polymer ground in a Wiley mill through a 20 mesh screen and dried for 24 hours at 50° C. at 0.1 mm Hg. The resultant polymers from tubes 1 and 2 were formed in 86% and 89% conversion and had I.V.'s of 0.33 and 0.27, respectively. The present conversion to polymer was obtained by dividing the weight of polymer after drying by the weight of polymer before drying. I.V. means the inherent viscosity of a solution of 0.5 g of dried polymer/100 ml of hexafluoroacetone sesquihydrate, measured at 30° C.

Into a three neck 100 ml round bottom flask equipped with a glass shaft and Teflon ® paddle stirrer, attached to a stirring motor and a gas inlet tube connected to an argon cylinder, was added 7.0 g of the 0.33 I.V. poly L(—) lactide described above. The flask was flushed with argon gas for 15 minutes. The flush was maintained throughout the polymerization. The flask was placed in a 190° C. oil bath. The pot contents reached 180°±2° C. within 15 minutes. Then 3.5 g of glycolide was added with stirring and the oil bath temperature was adjusted to keep the temperature of the pot contents at 180°±2° C. for 30 minutes with continuous stirring. The temperature of the oil bath was then raised so that during 30 minutes the temperature of the pot contents reached 220°±2° C. Then the remainder of the glycolide, 31.5 g, was added and the temperature of the pot contents was maintained at 220°±2° C. for 1½ hours with continuous stirring. At that time the oil bath was removed, the stirring was stopped, and the pot contents were allowed to cool to approximately room temperature under the argon flush. This flush was then stopped. The glass flask was then broken and the polymer was removed and ground in a Wiley mill through a 20 mesh screen. A portion (3.0 g) of the ground polymer was dissolved in 60 ml of hexafluoroacetone sesquihydrate (HFAS) at 60° C. The polymer was precipitated by dripping this solution into 600 ml of methanol with stirring. The polymer was collected by filtration and extracted with acetone in a Soxhlet extractor for 2 days to remove the residue of fluorinated solvent. The polymer was then dried in a vacuum oven overnight at 50° C. at 0.1 mm Hg. The yield of polymer was 95%. The I.V. in HFAS was 0.77. The mole percent of the lactic acid units in the polymer chain as determined by NMR was 8.8. The melting point as determined from the peak endotherm observed in a differential thermal analysis (D.T.A.) apparatus was 218° C.

A second two-stage copolymer was prepared as follows. Into a three neck 100 ml round bottom flask equipped with a glass shaft and a Teflon ® paddle stirrer attached to a stirring motor, and a gas inlet tube connected to an argon cylinder, was added 4.0 g of the poly L(—) lactide whose I.V. was 0.27, with stirring. This was flushed with argon gas for 15 minutes. This argon gas flush was maintained throughout the following polymerization. The flask was placed in a 190° C. oil bath. The pot contents reached 180°±2° C. within 15 minutes. Then, 3.6 g of glycolide were added with stirring and the oil bath temperature was adjusted to keep the temperature of the pot contents at 180°±2° C. for 30 minutes with continuous stirring. The temperature of the oil bath was then raised so that at the end of 30 minutes the temperature of the pot contents reached 220°±2° C. Then, 31.4 g of glycolide was added and the temperature of the pot contents was maintained at 220°±2° C. for 1½ hours with continuous stirring. At this time the oil bath was removed, the stirring was stopped and the pot contents were allowed to cool to approximately room temperature under the argon flush. The flush was then stopped. The glass flask was broken and the polymer was removed and ground in a Wiley mill through a 20 mesh screen. 3.0 g of this polymer were dissolved in 60 ml of 60° C. hexafluoroacetone sesquihydrate (HFAS) and the polymer was precipitated by dripping this solution into 600 ml of methanol with stirring. The polymer was collected by filtration and extracted with acetone in a Soxhlet extractor for 2 days. The polymer was then dried in a vacuum oven overnight at 50° C. at 0.1 mm Hg. The yield of polymer was 95%. The I.V. in HFAS was 0.82. The mole precent of lactic acid units in the polymer as determined by NMR was 5.9. The melting point as determined by the peak endotherm observed in a D.T.A. apparatus was 219° C.

EXAMPLE 3

A sample of poly L(—) lactide was prepared by the procedure of Examples 1-2 except that it was formed in 98% conversion with a 0.5 I.V. using 1.2 mg of Sn $Cl_2.2H_2O$ and 7.5 mg of lauryl alcohol. Into a three neck 100 ml round bottom flask equipped with a glass shaft and a Teflon ® paddle stirrer attached to a stirring motor and a gas inlet tube attached to an argon cylinder, was added 10.0 g of the poly L(—) lactide. This was flushed with argon for 15 minutes. This argon flush was maintained through the following polymerization. The flask was placed in a 190° C. oil bath. The pot contents reached 180°±2° C. with 15 minutes. Then 2 g of glycolide was added with stirring and the oil bath temperature was adjusted to keep the temperature of the pot contents at 180°±2° C. for 30 minutes with continuous stirring. The temperature of the oil bath was then raised so that at the end of 30 minutes the temperature of the pot contents reached 220°±2° C. Then, 18.0 g of glycolide were added and the temperature of the pot contents was maintained at 220°±2° C. for 1½ hours with continuous stirring. At this time the oil bath was removed, the stirring was stopped and the pot contents were allowed to cool to approximately room temperature under argon flush. This flush was then stopped. The glass flask was broken and the polymer was ground up in a Wiley mill through a 20 mesh screen.

20.0 g of this polymer was dissolved in 400 ml of 60° C. hexafluoroacetone sesquihydrate (HFAS) and the polymer was precipitated by dripping this solution into 4,000 ml of methanol with stirring. The polymer was collected by filtration and extracted with acetone in a Soxhlet extractor for 2 days. The polymer was then dried in a vacuum oven overnight at 50° C. at 0.1 mm Hg. The yield of polymer was 72%. The I.V. in HFAS was 0.60. The mole percent of lactic acid units in the polymer as determined by NMR was 33. The melting point as determined from the peak endotherm observed in a differential thermal analysis (D.T.A.) apparatus was 219° C.

EXAMPLE 4

Into a three neck 100 ml round bottom flask equipped with a glass shaft and a Teflon ® paddle stirrer attached to a stirring motor and a gas inlet tube attached to an argon cylinder, was added 6.0 g of a 0.29 I.V. poly L(−) lactide prepared as in Example 3 except that a heating period of 1.5 hours at 200° C. was used. The flask was flushed with argon for 15 minutes. This argon flush was maintained throughout the following polymerization. The flask was placed in a 200° C. oil bath and the bath temperature was raised until the temperature of the pot contents reached 200°±2° C. This occurred within 15 minutes. Then, 48.0 g of glycolide were added with stirring and the temperature of the oil bath was raised until the temperature of the pot contents was 225°±2° C. This occurred within 30 minutes. Stirring was continued for 1½ hours at this temperature. Then, 6.0 g of L(−) lactide were added (with stirring of the pot contents) and stirring was continued 1½ hours at this temperature. At this time, the oil bath was removed, the stirring was stopped and the pot contents were allowed to cool to approximately room temperature under the argon flush. This flush was then stopped. The glass flask was broken and the polymer was removed and ground in a Wiley mill through a 20 mesh screen. 5.0 g of this polymer were dissolved in 100 ml of hexafluoroacetone sesquihydrate (HFAS) and the polymer was precipitated by dripping this solution in 1,000 ml of methanol with stirring. The polymer was collected by filtration and extracted with acetone in a Soxhlet extractor for 2 days. The polymer was dried in a vacuum oven overnight at 50° C. at 0.1 mm Hg. The yield of polymer was 82%. The I.V. in HFAS was 0.81. The mole percent of lactic acid units in the polymer chain as determined by NMR was 11.2. The melting point as determined from the peak endotherm in a differential thermal analysis (D.T.A.) apparatus was 216° C.

EXAMPLE 5

Into a three neck 100 ml round bottom flask equipped with a glass shaft and a Teflon ® paddle attached to a stirring motor and a gas inlet tube attached to an argon cylinder, was added 4.5 g of poly(epsilon-caprolactone) whose I.V. was 0.42. The poly(epsilon-caprolactone) polymer was prepared as in Example 1 except that 8.0 mg of $SnCl_2.2H_2O$ and 500 mg of lauryl alcohol were employed and epsilon-caprolactone was used in place of the L(−) lactide. The flask was flushed with argon for 15 minutes. The argon flush was maintained throughout the following polymerization. The flask was placed in a 190° C. oil bath. The pot contents reached 180°±2° C. within 15 minutes. Then, 1.35 g of glycolide were added with stirring and the oil bath temperature was adjusted to keep the temperature of the pot contents at 180°±2° C. for 30 minutes with continuous stirring. The temperature of the oil bath was then raised so that at the end of 30 minutes the temperature of the pot contents was 220°±2° C. Then, 12.15 g of glycolide were added with stirring and the temperature of the pot contents was maintained at 220°±2° C. for 1½ hours with continuous stirring. At this time the oil bath was removed, the stirring was stopped and the pot contents were allowed to cool to approximately room temperature under the argon flush. This flush was then stopped. The glass flask was broken and the polymer was removed and ground in a Wiley mill through a 20 mesh screen. 4.0 g of this polymer was dissolved in 80 ml of 60° C. HFAS and the polymer was precipitated by dripping this solution into 1000 ml of methanol with stirring. The polymer was collected by filtration and extracted with acetone in a Soxhlet extractor for 2 days. The polymer was then dried overnight in a vacuum oven at 50° C. at 0.1 mm Hg. The yield of polymer was 73%. The I.V. in HFAS was 0.77. The mole percent of epsilon-hydroxy caproic acid units in the polymer chain as determined by NMR was 12.3. This corresponds to 12.1 weight percent caprolactone units. The melting point as determined from the peak endotherm in a differential thermal analysis (D.T.A.) apparatus was 218° C.

EXAMPLE 6

Into a three neck 100 ml round bottom flask equipped with a glass shaft and a Teflon ® paddle attached to a stirring motor and a gas inlet tube attached to an argon cylinder was added 7.0 g of poly(trimethylene carbonate) whose I.V. was 0.34. The poly(trimethylene carbonate) was prepared by the procedure of Example 1 except that trimethylene carbonate was used in place of the L(−) lactide and 4.0 mg of $SnCl_2.2H_2O$ was used with 250 mg of lauryl alcohol; the conversion was 48%.

The flask was flushed with argon for 15 minutes. The argon flush was maintained throughout the following polymerization. The flask was placed in a 190° C. oil bath. The pot contents reached 180°±2° C. within 15 minutes. Then, 3.5 g of glycolide were added with stirring and the oil bath temperature was adjusted to keep the temperature of the pot contents at 180°±2° C. for 30 minutes with continuous stirring. The temperature of the oil bath was then raised so that at the end of 30 minutes the temperature of the pot contents was 220°±2° C. Then, 31.5 g of glycolide were added with stirring and the temperature of the pot contents was maintained at 220°±2° C. for 1½ hours with continuous stirring. At this time the oil bath was removed, the stirring was stopped and the pot contents were allowed to cool to approximately room temperature under the argon flush. This flush was then stopped. The glass flask was broken and the polymer was removed and ground in a Wiley mill through a 20 mesh screen. 5.0 g of this polymer were dissolved in 100 ml of 60° C. HFAS and the polymer was precipitated by dripping this solution into 1,000 ml of methanol with stirring. The polymer was collected by filtration and extracted with acetone in a Soxhlet extractor for 2 days. The polymer was dried overnight in a vacuum oven at 50° C. at 0.1 mm Hg. The yield of polymer was 86%. The I.V. in HFAS was 0.64. The mole percent of units derived from trimethylene carbonate in the polymer chain as determined by NMR was 16.4. This figure corresponds to 14.7 weight percent trimethylene carbonate units. The melting point as determined from the peak endotherm in a differential thermal analysis (D.T.A.) apparatus was 218° C.

EXAMPLE 7

Trimethylene carbonate (39 g.), $SnCl_2.2H_2O$ (3.3 mg.) and lauryl alcohol (0.133 g.) were added to a stirred reactor which had been preheated to 153° C. under a stream of nitrogen. The temperature was increased over a 30 minute period to 180° C. After stirring an additional 30 minutes at that temperature a 2.5 g. sample was withdrawn and glycolide (17 g.) was added. The temperature was then raised over a 30 minute period to 223° C. After stirring the mixture for 45 minutes at this temperature, more glycolide (153 g.) was added. Stirring was continued for one hour at this temperature at which point the polymer was discharged. The polymer was cooled and ground finely enough to pass through a 10 mesh screen, and was then dried for 48 hours at 140° C. (0.25 mmHg).

The 2.5 g sample of poly(trimethylene carbonate) removed at 180° C. was dissolved in methylene chloride. The solution was added dropwise to methanol and the precipitated polymer was collected and dried 24 hours at 40° C. (0.25 mgHg). The resulting homopolymer had an inherent viscosity of 1.32 (30° C., 0.5% solution) in H.F.A.S.

The inherent viscosity of the final copolymer was 0.81. The concentration of trimethylene carbonate units in the copolymer was found by NMR analysis to be 17 mole percent or 15% by weight. Using differential scanning calorimetry, the glass transition temperature was found to be 32° C. and the peak of the melting endotherm was found at 216° C.

EXAMPLE 8

The copolymer of Example 7 was extruded at a temperature of 230° C. at the rate of 0.5 lbs/hr through a 30 mil capillary having a length to diameter ratio of 4 to 1. The extrudate was passed through a water quench bath at room temperature and collected on a bobbin at the rate of 200 feet per minute.

The resulting extrudate was then drawn through a hot air chamber set at 40° C. at a rate of 10 feet per minute and a draw ratio of 5.2X, to form a monofilament falling in the USP size 6/0 range.

The physical properties of the drawn fiber were:

| | |
|---|---|
| Straight Pull Tensile Strength: | 98,600 psi |
| Straight Pull Elongation At Break: | 35% |
| Knot Pull Strength: | 78,600 psi |
| Modulus: | 1,300,000 psi |
| Diameter: | 0.096mm |

EXAMPLE 9

Samples of the monofilament of Example 8 were implanted subcutaneously in rats. After 21 days the samples were removed and their straight pull tensile strength was measured on an Instron Universal Testing Machine Model 1125 (Instron Corp., Canton, MA., U.S.A.). The samples retained, as an average, 45% of their original straight pull tensile strength.

EXAMPLE 10

Trimethylene carbonate (20 g), $SnCl_2.2H_2O$ (4 mg.) and lauryl alcohol (0.199 g) were added to a stirred reactor which had been preheated to 140° C. The reaction mixture was stirred for two hours at this temperature under a nitrogen atmosphere at which time a vacuum of 50 mm. Hg was applied and maintained for 30 minutes. The vacuum was released with nitrogen and glycolide (180 g), preheated at 140° C., was added under nitrogen flow. The reactor was then heated over a 30 minute period to a temperature of 220° C. The temperature was held at 220°-222° C. for an additional 45 minutes at which point the polymer was discharged. The polymer was cooled, cut into small pieces and dried for 24 hours at 130° C. (1 mmHg).

The inherent viscosity of the polymer was found to be 0.86, measured at 30° C. in a 0.5% solution in hexafluoroacetone sesquihydrate (HFAS). The concentration of trimethylene carbonate units in the copolymer was found to be 9 mole percent by NMR. This figure corresponds to 8 weight percent trimethylene carbonate units. Using differential scanning colorimetry, the glass transition temperature was found to be 37° C.; the melting range was 196°–225° C., the peak of the melting endotherm occurred at 221° C. and $\Delta H_f$ (the heat of fusion) was 17.6 cal./g. A portion of the polymer (130 g) was further treated by heating for three days at 180° C. (0.2 mmHg) under a nitrogen flow of 2 cubic feet per hour. The final product weighed 120 g, had an inherent viscosity of 0.96 and contained 8.3 mole percent (7.4 weight percent) of trimethylene carbonate units.

EXAMPLE 11

The copolymer of Example 10 was extruded at a temperature of 230° C. through a 60 mil capillary having a length to diameter ratio of 4 to 1. The extrudate was passed through a water quench bath at room temperature and collected on a bobbin at the rate of 50 feet per minute. The resulting extrudate was then drawn 8X through a hot air chamber set at 50° C. The physical properties of the drawn fiber were:

| | |
|---|---|
| Straight Pull Tensile Strength: | 71,500 psi |
| Straight Pull Elongation At Break: | 31% |
| Knot Pull Strength: | 54,400 psi |
| Modulus: | 1,280,000 psi |
| Diameter: | 0.164 mm |

EXAMPLE 12

Trimethylene carbonate (98.0 g.), $SnCl_2.2H_2O$ (1.9 mg.) and lauryl alcohol (74.8 mg.) were added to a stirred reactor which had been preheated to 172° C. under a stream of nitrogen. The temperature was raised to 186° C. over a 1 hour period. A 3.6 g. sample was withdrawn and glycolide (14.0 g.) was added. The temperature was raised over a 10 minute period to 200° C. More glycolide (90.0 g) was added. The temperature was then raised to 221° C. over the next 25 minutes at which point the polymer was discharged. The polymer was cooled and ground finely enough to pass through a 10 mesh screen, and was then dried for 48 hours at 130° C. (<1 mmHg).

The 3.6 g. sample removed at 186° C. had an inherent viscosity of 2.21 (30° C., 0.5% solution) in $CH_2Cl_2$.

The inherent viscosity of the final copolymer was 0.94 in H.F.A.S. The concentration of trimethylene carbonate units in the copolymer was found by NMR analysis to be 48.5 mole percent of 45.3% by weight. Using differential scanning calorimetry, the glass transition temperatures were found to be −5° and 34° C. and the peak of the melting endotherm was found at 216° C.

EXAMPLE 13

Trimethylene carbonate (125.0 g.), $SnCl_2.2H_2O$ (1.9 mg.) and lauryl alcohol (74.8 mg.) were added to a stirred reactor which had been preheated to 153° C. under a stream of nitrogen. The temperature was raised to 192° C. over a 75 minute period. A 2.6 g. sample was withdrawn and glycolide (10.0 g) added. The temperature was raised to 198° C. over 10 minutes at which point more glycolide (85.0 g.) was added. The temperature was then raised to 220° C. over 10 minutes and the polymer discharged. The polymer was cooled and ground finely enough to pass through a 10 mesh screen, and was then dried for 48 hours at 130° C. (<1 mmHg).

The 2.6 g sample withdrawn at 192° C. had an inherent viscosity of 1.28 (30° C., 0.5% solution) in $CH_2Cl_2$.

The inherent viscosity of the final copolymer was 1.07 as measured in H.F.A.S. The concentration of trimethylene carbonate units in the copolymer was found by NMR analysis to be 57.4 mole percent or 54.2% by weight. Using differential scanning calorimetry, the glass transitions were found to be 2° and 29° C. and the peak of the melting endotherm was found at 212° C.

EXAMPLE 14

The copolymer of Example 12 was extruded essentially as described in Example 8. The physical properties of the drawn monofilament were:

| | |
|---|---|
| Straight Pull Tensile Strength: | 26,000 psi |
| Straight Pull Elongation At Break: | 16% |
| Knot Pull Strength: | 14,000 psi |
| Modulus: | 479,000 psi |
| Diameter: | 0.286 mm |

EXAMPLE 15

The copolymer of Example 13 was extruded essentially as described in Example 8. The physical properties of the drawn monofilament were:

| | |
|---|---|
| Straight Pull Tensile Strength: | 26,000 psi |
| Straight Pull Elongation At Break: | 50% |
| Knot Pull Strength: | 28,000 psi |
| Modulus: | 203,000 psi |
| Diameter: | 0.265 mm |

EXAMPLE 16

Samples of the monofilament of Example 14 were implanted subcutaneously in rats. After 42 days the samples were removed and their straight pull tensile strength was measured as described in Example 9. The samples retained, as an average, 38% of their original straight pull tensile strength.

EXAMPLE 17

Samples of the monofilament of Example 15 were implanted subcutaneously in rats. After 42 days the samples were removed and their straight pull tensile strength was measured as described in Example 9. The samples retained, as an average, 35% of their original straight pull tensile strength.

EXAMPLE 18

L(−) lactide (1612 g), $SnCl_2.2H_2O$ (0.204 g) and lauryl alcohol (4.77 g) were added to a stirred reactor which had been preheated to 140° C. The reactants were heated with stirring under a nitrogen atmosphere over a 30 minute period to 200° C. and then held at that temperature for 2 hours.

The reactor was evacuated to a pressure of 50 mmHg and the mixture was stirred for 30 minutes during which time the temperature of the mixture was allowed to fall to 180° C.

Atmospheric pressure was restored by introducing nitrogen into the reaction vessel and the temperature was raised to 200° C. over a 5 minute period. The molten glycolide (5198 g) preheated to 100° C. was added and the temperature was raised over a 15 minute period to 225° C. and held at this temperature for an additional 20 minutes.

The contents of the reactor were discharged and the polymeric mass was broken up after it had cooled to room temperature. The polymer was then ground and vacuum dried at 8–10 mmHg for 11 hours at 140° C. to remove all volatiles preparatory to spinning and determining the polymer's viscosity.

The inherent viscosity of the polymer was determined to be 1.14, measured at 30° C. in a 0.5% solution in hexafluoroacetone sesquihydrate. The mole % of lactic acid units in the finished polymer was determined to be 20.3% by NMR. The melting range of the product was determined to be 215°–223.5° C. using a hot stage polarizing microscope.

A portion of the dried polymer was added to the feed hopper of a small continuous extruder operating at about 230° C. The extruder was equipped with a die having a 60 mil cylindrical orifice and a length to diameter ratio of 4 to 1. The extrudate was water quenched and collected at 44 feet per minute. It was then drawn to about 4.5 times its original length at 55° C. in a hot air draw unit. A sample of glycolide homopolymer having a 1.05 I.V. was extruded and drawn in the same way and then post-treated along with the above copolymer fiber, for 3 hours at 135° C. at a pressure of 1 mmHg.

The copolymer fiber which was 2.45 mils in diameter was found to have exceptional tensile-strength retention properties (34,600 p.s.i.) in an accelerated strength retention test and very good initial tensile strength (96,500 p.s.i.) notwithstanding its high comonomer content (20.3 mole%). In the contrast, the initial strength of the homopolymer fiber which was 2.10 mils in diameter was 140,000 p.s.i. and the counterpart strength retained in an accelerated test was 25,300 p.s.i.

As mentioned above, it is believed that such copolymeric polyesters are characterized by microphase separations having spherical domains in the molten state, prior to orientation wherein the chain segments composed of lactic acid units are overlapped with themselves in a matrix of glycolic acid units. It is believed that polyesters having such microphase separation would exist where the mole percentage of L(−) lactide incorporated into the polymer chains ranged up to about 25 percent. From about 25 percent to about 40 percent lactic acid units it is believed that cylindrical domains of lactic acid units would predominate. This would likewise be the case where the lactic acid units prevailed on both ends of the polyester chains as a result of sequentially and consecutively polymerizing L(—) lactide, glycolide and then L(—) lactide.

Although the geometry of the domains in the molten state is speculative, evidence for the existence of phase separation or precipitation of the polymers may be seen by comparing their melting points with that of the homopolymer of the major component.

Accordingly, preferred surgical articles prepared in accordance with the present invention are sterile synthetic absorbable surgical sutures prepared from a lactide polyester said polyester being composed of a copolymer having cylindrical or more preferably spherical dominions of L(—) lactide units in a matrix of glycolide units. The polyesters employed can have the relative quantities of glycolide units and L(—) lactide units indicated above. The sutures may be in the form of a sterile surgical needle and suture combination. Conventional suture contructions and sterilization methods may be used. Preferably a monofilament or polyfilamentary braided polyester yarn is crimped into the butt of a surgical needle and the needled suture is then sterilized using a toxicant such as ethylene oxide. Polyesters formed by sequentially and consecutively polymerizing L(—) lactide and glycolide are most preferred for use therein.

While the surgical articles of the present invention are generally useful in conventional manners for retaining living tissue in a desired location and relationship during a healing process by positioning and emplacing living tissue therewith, as in ligation of blood vessels, the needled sutures are especially adapted for the closing of wounds of living tissue by sewing together the edges thereof using conventional suturing techniques.

We claim:

1. A sterile surgical article fabricated from a synthetic absorbable copolymer formed by copolymerizing glycolide as the predominant monomer with a cyclic ester monomer other than glycolide, the improvement comprising employing sequential addition of the monomers in the polymerization wherein said glycolide monomer, said cyclic ester monomer, or a combination of said monomers is substantially completely polymerized before the addition of the other monomer or said combination.

2. An article according to claim 1 wherein said cyclic ester monomer is L(—) lactide.

3. An article according to claim 1 wherein said cyclic ester monomer is selected from the group consisting of lactones, oxalates or carbonates.

4. An article according to claim 3 wherein said cyclic ester monomer is 1,3-dioxan-2-one.

5. An article according to claim 1 wherein said cyclic ester monomer is epsilon-caprolactone.

6. An article according to claim 1 in the form of a suture or ligature.

7. An article according to claim 6 in the form of a needle and suture combination.

8. A sterile surgical article fabricated from a synthetic absorbable copolymer comprising a proportion of sequential units having the formula:

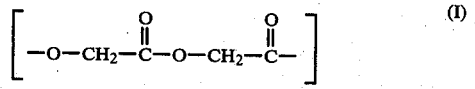

and a proportion of sequential units having the formula:

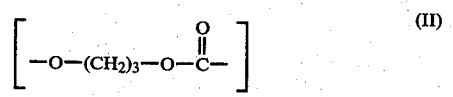

wherein formula (II) consists of up to about 50% by weight.

9. An article of claim 8 having a melting point of about 217° C. to 221° C. as described by the peak in a differential scanning calorimeter operating at a heating rate of 10° C. per minute.

10. An article of claim 9 having an inherent viscosity of about 0.5 dl/g. to 2 dl/g.

11. An article of claim 10 having an inherent viscosity of about 0.7 dl/g to 1.2 dl/g.

12. An article of claim 8 or 9 or 11 wherein formula (II) consists of up to about 35% by weight.

13. An article of claim 12 wherein formula (II) consists of between about 10% to 20% by weight.

14. An article according to claim 8 in the form of a suture or ligature.

15. An article according to claim 14 in the form of a needle and suture combination.

16. A method of retaining living tissue in a desired relationship during a healing process by positioning and emplacing living tissue with a sterile surgical article of claim 8.

17. A method of closing a wound of living tissue which comprises sewing the edges of the wound with a needled suture of claim 15.

* * * * *